US009757273B2

(12) United States Patent
Heeren (10) Patent No.: US 9,757,273 B2
(45) Date of Patent: Sep. 12, 2017

(54) TISSUE-SENSING VITRECTOMY SURGICAL SYSTEMS AND METHODS

(71) Applicant: Novartis AG, Basel (CH)

(72) Inventor: Tammo Heeren, Aliso Viejo, CA (US)

(73) Assignee: Novartis AG, Lichtstrasse, Basel (CH)

( * ) Notice: Subject to any disclaimer, the term of this patent is extended or adjusted under 35 U.S.C. 154(b) by 648 days.

(21) Appl. No.: 14/136,227

(22) Filed: Dec. 20, 2013

(65) Prior Publication Data

US 2015/0173948 A1      Jun. 25, 2015

(51) Int. Cl.
*A61F 9/007*       (2006.01)
*A61B 17/00*       (2006.01)

(52) U.S. Cl.
CPC ...... *A61F 9/00736* (2013.01); *A61F 9/00763* (2013.01); *A61B 2017/00022* (2013.01); *A61B 2017/00026* (2013.01); *A61B 2017/00057* (2013.01)

(58) Field of Classification Search
CPC .............. A61F 9/00736; A61F 9/00745; A61F 9/00754; A61F 9/00763; A61B 2017/00057; A61B 2017/00026; A61B 2017/00022; A61B 2018/00773; A61B 2562/02; A61B 2562/0233; A61B 2562/0238

See application file for complete search history.

(56) References Cited

U.S. PATENT DOCUMENTS

| | | | | |
|---|---|---|---|---|
| 3,884,238 A | * | 5/1975 | O'Malley | ........... A61F 9/00763 606/107 |
| 4,548,205 A | * | 10/1985 | Armeniades | ............. A61B 3/16 600/488 |
| 5,047,008 A | * | 9/1991 | de Juan, Jr. | ......... A61F 9/00763 600/564 |
| 5,195,375 A | | 3/1993 | Tenerz et al. | |
| 5,520,633 A | * | 5/1996 | Costin | ................. A61M 1/0031 601/2 |
| 5,669,876 A | | 9/1997 | Schechter et al. | |

(Continued)

FOREIGN PATENT DOCUMENTS

| | | |
|---|---|---|
| EP | 0 424 687 A1 | 5/1991 |
| GB | 2111390 A | 7/1983 |

(Continued)

OTHER PUBLICATIONS

International Search Report and Written Opinion issued for PCT/US2014/067314 dated Feb. 19, 2015, 11 pgs.

*Primary Examiner* — Jocelin Tanner (57) ABSTRACT

A device for removing a tissue from an eye of a patient is disclosed, comprising a housing, a cutter, and an actuator. The cutter comprises an outer cutting tube coupled to the housing, an outer port formed in the outer cutting tube, an inner cutting tube slidable along the longitudinal axis within the outer cutting tube between a retracted position proximal to the outer port and an extended position distal to the outer port, and a tissue sensor positioned on the cutter and configured to measure a characteristic of the tissue received within the outer port to identify when nontarget tissue enters the outer port. The actuator within the housing is configured to reciprocate the inner cutting member between the retracted position and the extended position to open and close the outer port and cut the tissue.

11 Claims, 5 Drawing Sheets

(56) References Cited

U.S. PATENT DOCUMENTS

| | | | |
|---|---|---|---|
| 5,928,158 A * | 7/1999 | Aristides | A61B 17/32 600/547 |
| 6,162,182 A | 12/2000 | Cole | |
| 6,214,018 B1 * | 4/2001 | Kreizman | A61B 90/17 600/429 |
| 6,527,736 B1 | 3/2003 | Attinger et al. | |
| 7,338,434 B1 * | 3/2008 | Haarstad | A61B 17/00234 600/201 |
| 7,837,660 B2 | 11/2010 | Jones et al. | |
| 8,109,937 B2 | 2/2012 | Huculak et al. | |
| 8,246,580 B2 | 8/2012 | Hopkins et al. | |
| 2002/0058956 A1 * | 5/2002 | Honeycutt | A61B 17/32075 606/159 |
| 2002/0111634 A1 * | 8/2002 | Stoianovici | A61B 90/50 606/129 |
| 2002/0170399 A1 | 11/2002 | Gass et al. | |
| 2004/0246132 A1 | 12/2004 | Kuan | |
| 2005/0059965 A1 * | 3/2005 | Eberl | A61B 18/1492 606/41 |
| 2005/0145080 A1 | 7/2005 | Voigtlaender | |
| 2005/0171446 A1 * | 8/2005 | Krivitski | A61B 17/22 600/504 |
| 2008/0082078 A1 | 4/2008 | Berlin | |
| 2010/0081964 A1 | 4/2010 | Mark et al. | |
| 2010/0156646 A1 | 6/2010 | Cull et al. | |
| 2010/0228194 A1 * | 9/2010 | Freeman | A61B 5/053 604/117 |
| 2010/0280409 A1 * | 11/2010 | Mark | A61B 10/0275 600/567 |
| 2011/0106102 A1 * | 5/2011 | Balicki | A61B 3/1005 606/130 |
| 2011/0118729 A1 | 5/2011 | Heeren et al. | |
| 2011/0295191 A1 * | 12/2011 | Injev | A61F 9/00745 604/22 |
| 2011/0295293 A1 | 12/2011 | Agahi et al. | |
| 2011/0308365 A1 | 12/2011 | Chiu et al. | |
| 2012/0158029 A1 * | 6/2012 | Underwood | A61B 17/32002 606/171 |
| 2012/0283563 A1 * | 11/2012 | Moore | A61B 10/0275 600/437 |
| 2012/0296238 A1 * | 11/2012 | Chernov | A61B 18/1442 601/2 |
| 2013/0144317 A1 | 6/2013 | Valencia | |

FOREIGN PATENT DOCUMENTS

| | | |
|---|---|---|
| WO | WO 02/26016 A2 | 4/2002 |
| WO | WO 03/047653 A1 | 6/2003 |
| WO | 2008080148 A2 | 7/2008 |
| WO | WO 2015/080851 A1 | 6/2015 |

* cited by examiner

TISSUE-SENSING VITRECTOMY SURGICAL SYSTEMS AND METHODS

BACKGROUND

The present invention pertains to vitrectomy probes, systems, and methods. More particularly, but not by way of limitation, the present invention pertains to the monitoring of vitrectomy probes and their operating environments.

Microsurgical procedures frequently require precision cutting and/or removing various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. These cutting probes typically include a hollow outer cutting member, a hollow inner cutting member arranged coaxially with and movably disposed within the hollow outer cutting member, and a port extending radially through the outer cutting member near the distal end thereof. Vitreous humor and/or membranes are aspirated into the open port, and the inner member is actuated, closing the port. Upon the closing of the port, cutting surfaces on both the inner and outer cutting members cooperate to cut the vitreous and/or membranes, and the cut tissue is then aspirated away through the inner cutting member.

Many complications can arise during procedures requiring the use of these microsurgical cutting probes. Some of these complications may arise because of the nature of the procedures. For example, during removal of vitreous humor, the surgeon may inadvertently aspirate and cut typically non-target ocular tissues, such as the retina.

The present disclosure is directed to addressing one or more of the deficiencies in the prior art.

SUMMARY

In one exemplary aspect, the present disclosure is directed to a device for removing a tissue from an eye of a patient during a medical procedure, the device comprising a housing, a cutter extending from a distal end of the housing along a longitudinal axis, a tissue sensor positioned on the cutter, and an actuator. In one aspect, the cutter comprises an inner cutting tube that is disposed within an outer cutting tube coupled to the housing. In one aspect, there is an outer port formed in the outer cutting tube that comprises an aperture extending from an outer surface to an inner surface of the outer cutting tube. The outer port is sized to receive the tissue. The inner cutting tube has a distal tube end slidable along the longitudinal axis between a retracted position proximal to the outer port and an extended position distal to the outer port. The tissue sensor is configured to measure a characteristic of the tissue received within the outer port to identify when nontarget tissue enters the outer port. The actuator is configured to reciprocate the inner cutting member to slide the distal tube end between the retracted position and the extended position to open and close the outer port and cut the tissue. In one aspect, the actuator positioned within the housing.

In one aspect, the device further includes an arresting mechanism disposed within the vitrectomy probe and coupled to the cutter, the arresting mechanism configured to halt the motion of the inner cutting tube.

In an additional exemplary aspect, the present disclosure is directed to a vitrectomy surgical system including a vitrectomy probe, an actuator, at least one tissue sensor coupled to the vitrectomy probe, and a processor. In one aspect, the vitrectomy probe includes a cutter comprising an outer cutting tube, an outer port disposed on the outer cutting tube, and an inner cutting tube disposed within the outer cutting tube, the inner cutting tube being movable relative to the outer cutting tube to cut tissue during a vitrectomy procedure. In one aspect, the actuator is configured to move the inner cutting tube relative to the outer cutting tube to open and close the outer port to cut tissue aspirated through the outer port into the outer cutting tube. In one aspect, the at least one tissue sensor is coupled to the vitrectomy probe adjacent the outer port, and is configured to measure a characteristic of the tissue aspirated through the outer port; and a processor communicatively coupled to the at least one tissue sensor and operable to control the movement of the inner cutting tube.

In another exemplary aspect, the present disclosure is directed to a method of treating an ophthalmic condition. The method comprises inserting a probe through a sclera into a vitreous chamber of a patient, the probe including a cutter comprising an inner cutting tube slidably disposed within an outer cutting tube, an outer port in the outer cutting tube, and at least one tissue sensor positioned near the outer port. In one aspect, the method further comprises measuring a tissue characteristic of tissue aspirated into the cutter with the at least one tissue sensor, and communicating the tissue characteristic to a processor operable to control the motion of the inner cutting tube relative to the outer cutting tube. In one aspect, the method comprises evaluating the measured tissue characteristic with a logic algorithm of the processor. The method comprises suspending the motion of the inner cutting tube based upon the measured tissue characteristic.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices and methods disclosed herein and together with the description, serve to explain the principles of the present disclosure.

These figures will be better understood by reference to the following detailed description.

DETAILED DESCRIPTION

For the purposes of promoting an understanding of the principles of the present disclosure, reference will now be made to the embodiments illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to systems and methods for sensing and characterizing tissue to prevent the inadvertent aspiration of various tissues during ophthalmic procedures, particularly procedures involving the removal of vitreous humor from a patient's eye. The inadvertent aspiration and cutting of necessary ocular tissue (e.g., retina) can adversely affect the outcome of such procedures and introduce unfortunate complications (such as, by way of non-limiting example, retinal tears or retinal detachment. In some aspects described herein, a vitrectomy probe includes tissue sensors to sense a characteristic of the aspirated tissue that enables the vitrectomy system to characterize the tissue as vitreous humor or another type of tissue. In some of the systems and methods described herein, the vitrectomy system includes an arresting mechanism that halts the cutting mechanism when the system, based on the sensed data, concludes that the aspirated tissue is not vitreous tissue. In some embodiments, the vitrectomy system includes processor logic that prevents initiation of the cutting mechanism when the system, based on the sensed data, concludes that the aspirated tissue is not vitreous tissue. In some aspects, the system includes an over-ride mechanism that allows the surgeon to temporarily disable the arresting mechanism and/or the processor logic, thereby enabling the vitrectomy probe to aspirate and cut non-vitreous tissue. The systems and methods disclosed herein may enable a surgeon to more effectively avoid inadvertent tissue aspirations that arise during vitrectomy procedures. By enabling the vitrectomy system to prevent or minimize the inadvertent aspiration and cutting of non-target (e.g., non-vitreous) tissues during a vitrectomy procedure, outcomes for patients may be improved. In one embodiment, the systems and methods described herein minimize the risk of inadvertently aspirating and cutting retinal tissue during removal of the vitreous.

Figure 1:
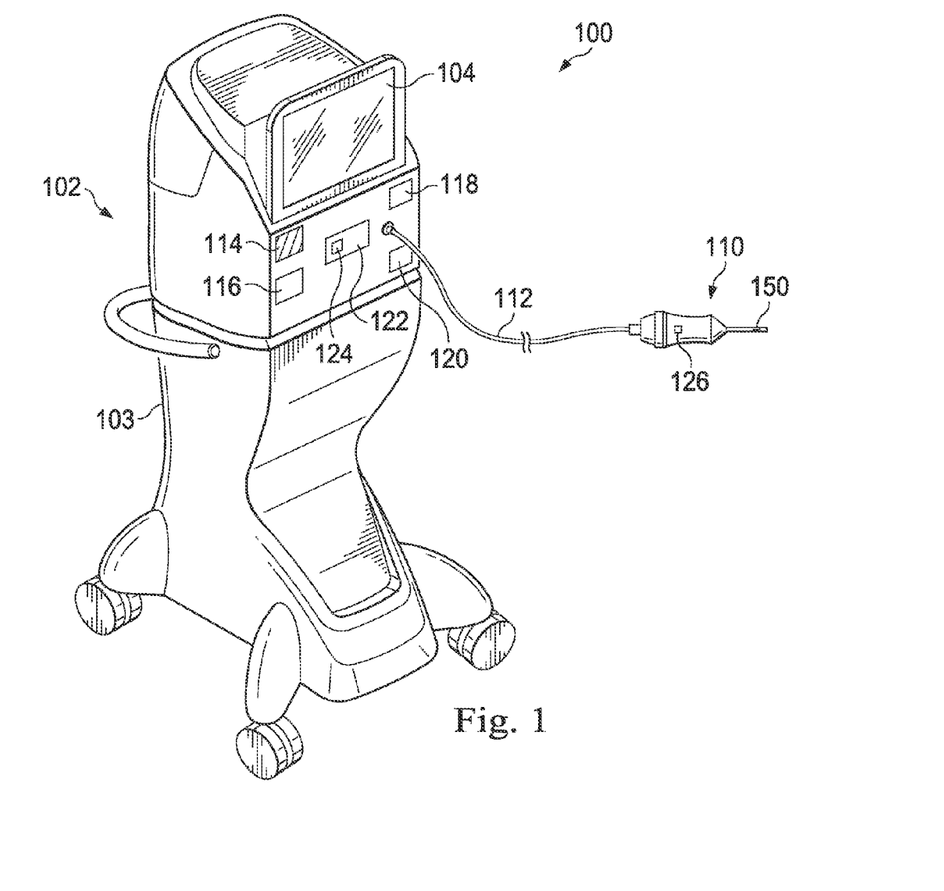
FIG. 1 is an illustration of a surgical system according to exemplary aspects of the present disclosure.

FIG. 1 illustrates a vitrectomy surgical system 100 according to an exemplary embodiment. The surgical system 100 includes a console 102 that has mobile base housing 103 and an associated display screen 104 showing data relating to system operation and performance during a vitrectomy surgical procedure. The surgical system 100 includes a vitrectomy probe system 110 that will be described in greater detail below. The console 102 of the surgical system 100 includes features that may allow for control of the vitrectomy probe system 110. For example, pneumatic and/or electrical supply lines 112 may couple the probe system 110 to the console 102. In some embodiments, the supply lines 112 may facilitate control and monitoring to the probe system 110 by also transmitting data between the probe system 110 and the console 102. In other embodiments, data may be transferred wirelessly between the probe system 110 and the console 102.

The console 102 further includes one or more processors 114 in communication with a memory 116. The processor 114 may have computer-instructions to control the probe system 110, display information on the screen 104, and receive and process input commands and data. In some embodiments, the surgical system 100 includes a data transmission module 118. In some embodiments, the surgical system 100 may include a network interface 120 for communication with a network. In the pictured embodiment, the surgical system 100 includes a user interface 122 that enables the user to input data and/or command signals. For example, in one embodiment, the user interface 122 may include an over-ride element 124 that allows the user to over-ride one or more logic functions of the processor 114. In some embodiments, the over-ride element comprises a button that may be manually depressed to activate the over-ride function. However, the over-ride element 124 may comprise any of a variety of ON/OFF switches, buttons, toggles, wheels, digital controls, touchscreen controls, or other user input devices. In some embodiments, the over-ride element 124 and/or another over-ride element 126 may be additionally or alternatively disposed on the probe system 110. In some embodiments, the over-ride element 124 and/or another over-ride element 126 may be additionally or alternatively disposed on an accessory control device, such as, by way of non-limiting example, a surgical footswitch, a remote control device, a touchscreen control device, and/or another computing device. These features facilitate control and monitoring of the probe system 110 during operation. Additionally, these features may facilitate the monitoring, data processing, and control for one or more tissue sensors 150 disposed on the probe system 110.

The processor 114 is typically an integrated circuit with power, input, and output pins capable of performing logic functions. For example, the processor 114 may perform logic functions based on inputs from the tissue sensor 150 to characterize the tissue type (e.g., determine whether the tissue is vitreous humor or another type of tissue) of the tissue drawn into the probe system 110. In some embodiments, the processor 114 controls the supply of power from a power source to the probe system 110 and/or signal commands to the probe system 110. In various embodiments, the processor 114 may be a targeted device controller or a microprocessor configured to control more than one component of the probe system 110 or a combination thereof. The processor 114 may include one or more programmable processor units running programmable code instructions for implementing the tissue characterization and vitrectomy control methods described herein, among other functions. For example, in some embodiments, the processor 114 controls the cutting mechanism of the probe system 110 by initiating, signaling, and/or triggering the movement of the cutting mechanism within the probe system 110 (e.g., the inner cutting tube 214 shown in FIG. 2).

The processor 114 may be wirelessly coupled to a computer and/or other types of processor-based devices suitable for a variety of ocular applications. In various embodiments, the processor 114 can receive input data from a user, the tissue sensor 150, the probe system 110, and/or various accessory devices via wireless or wired mechanisms. The processor 114 may use such input data to generate control signals to control or direct the operation of the probe system 110. In some embodiments, the processor 114 is in direct wireless communication with the probe system 110, and can receive data from and send commands to the probe system 110.

The memory 116, which is typically a semiconductor memory such as RAM, FRAM, or flash memory, interfaces with the processor 114. As such, the processor 114 can write to and read from the memory 116, and perform other common functions associated with managing semiconductor memory. For example, a series of tissue characterizations and/or command sequences can be stored in the memory 116.

The processor 114 and/or the memory 116 may also include software containing one or more algorithms defining one or more functions or relationships between command signals and input data (received from the user, the tissue sensor 150, and/or accessory devices). The algorithm may dictate activation or deactivation command protocols/signals (e.g., to the cutting mechanism of the probe system 110) depending on the received input data or mathematical derivatives thereof. In some embodiments, the algorithm may dictate activation or deactivation control signals affecting the cutting functionality of the probe system 110 when the input data from the sensor 150 indicates that the aspirated tissue in the probe system 110 is non-target tissue (e.g., retina) or target tissue (vitreous humor). For example, in some embodiments, the processor 114 includes logic algorithms that use input data from the tissue sensor 150 to determine whether the sensed tissue is target tissue that should be cut or is non-target tissue that should not be cut. If the processor, using the logic algorithm, determines that the tissue is non-target tissue, the processor 114 may not initiate, trigger, and/or signal the movement of the cutting mechanism of the probe system 110. If the processor 114 does not initiate the cutting mechanism of the probe system, the probe system 110 cannot cut tissue.

Thus, the processor 114 may be operable to selectively implement one or more control or logic algorithms to enable vitrectomy control, and, in particular, control of the cutting functionality of the probe system 110. In some embodiments, the processor 114 may be re-programmed to selectively implement one or more particular control algorithms. For example, in embodiments that include an over-ride element (e.g., the over-ride element 124 or the over-ride element 126), the processor 114 may be redirected to deactivate or temporarily ignore one or more control algorithms while the over-ride element is in an activated condition (e.g., while the over-ride element is in an ON position). In some embodiments, the over-ride element 124 (and/or 126) need not be continuously depressed or contacted to be in an ON position, but rather remains in an ON condition after one user input (e.g., after a single user input on a touchscreen button or a mechanical switch) to disable the control algorithms until the user actively turns OFF the over-ride element. In some embodiments, the over-ride element 124 (or 126) may be repeatedly depressed or contacted to temporarily disable the control algorithms only while the user is manually putting the over-ride element into the ON position. In some embodiments, the over-ride element 124 (and/or 126) is configured for both continuous deactivation and temporary disablement of the relevant control algorithms.

As mentioned above, in various embodiments, the probe system 110 may be operatively coupled to the console 102 (and, in particular, the processor 114) by way of wired or wireless communication mechanisms. Contemplated wireless communication methods include, by way of nonlimiting example, cooperating transmitters and receivers positioned on various components of the probe system 110 to allow remote communication with various components of the vitrectomy system 100. Thus, the data transmission module 118 may employ any of a number of different types of data transmission. In some embodiments, the data transmission module 118 may be activated to communicate the sensed data from the sensor 150 within the probe system 110 to the processor 114 and/or the memory 116. In some embodiments, control signals or program algorithms may be transmitted to the data transmission module 118 from the user interface 122 and/or an external device to adjust the treatment settings/algorithms.

Figure 2:
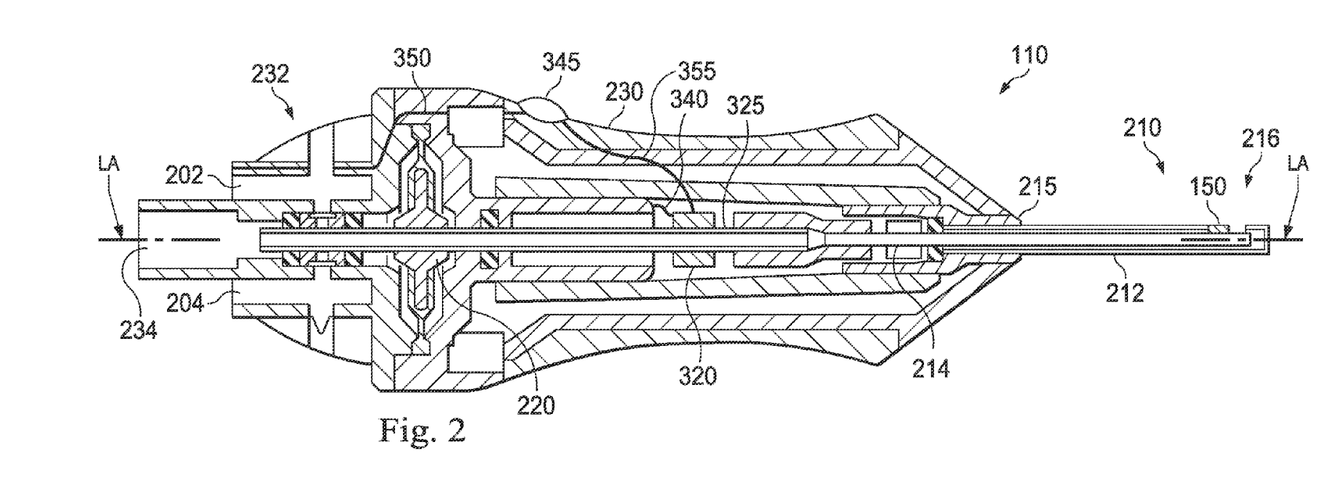
FIG. 2 is a cross-sectional illustration of a vitrectomy probe according to exemplary aspects of the present disclosure.

FIG. 2 shows a cross-sectional view of the vitrectomy probe system 110 previously shown in FIG. 1. In this example, the probe system 110 is a pneumatically driven system that operates by receiving pneumatic pressure alternating through first and second ports 202 and 204 over the supply lines 112 illustrated in FIG. 1. The probe system 110 includes as its basic components a cutter 210 and a probe actuator 220 shown here as a reciprocating air driven diaphragm 220, all partially encased by a probe housing 230. The probe housing 230 includes an end piece 232 at the probe proximal end with the first and second air supply ports 202, 204 and one suction port 234. The cutter 210 comprises an outer cutting tube 212 and an inner cutting tube 214. As can be seen, the cutter 210 extends distally from a distal end 215 of the housing 230 and includes a distal portion 216. The outer cutting tube 212 is coupled to the housing 230, and the inner cutting tube 214 is slidable within the outer cutting tube 212 along a longitudinal axis LA of the probe 110.

Figure 3:
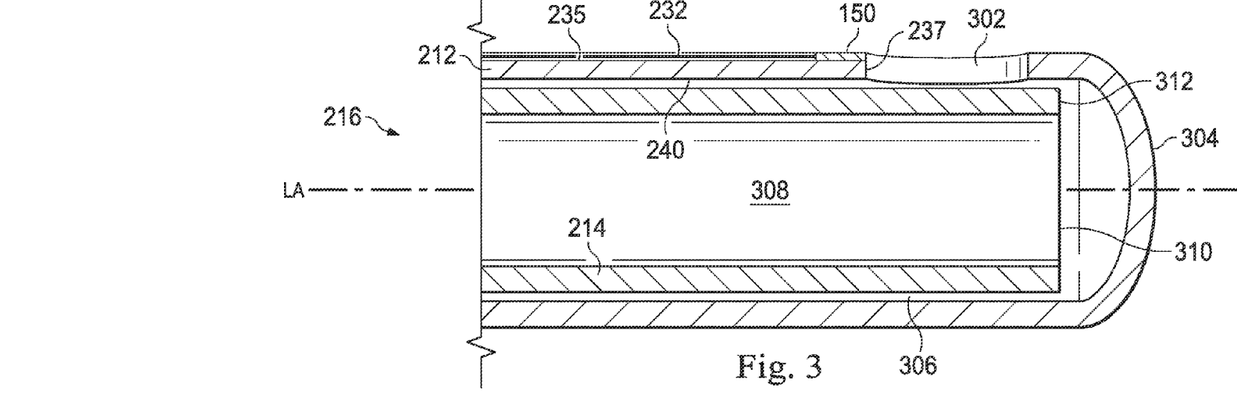
FIG. 3 is a close-up cross-sectional illustration of an exemplary distal portion of the cutter of the vitrectomy probe shown in FIG. 2 according to aspects of the present disclosure.

FIG. 3 is a cross-sectional view that provides additional detail regarding the distal portion 216 of the cutter 210 as seen in FIG. 2 and discussed above. The distal portion 216 includes an outer port 302 in the outer cutting tube 212 that receives tissue, such as ophthalmic tissue, during use. The outer port 302 is proximally offset from a closed end 304 of the distal portion 216. The inner cutting tube 214 is located within an inner channel 306 of the outer cutting tube 212. The outer port 302 is in fluid communication with the inner channel 306 of the outer cutting tube 212. The inner cutting tube 214 has an inner bore 308, an open distal end 310, and a cutting surface 312.

The inner bore 308 is in fluid communication with an aspiration line (not shown in FIGS. 2 and 3) coupled to the suction port 234 of FIG. 2. The aspiration line may be part of the supply lines 112 of FIG. 1. The suction port 234 connects the aspiration line to a vacuum (that provides an aspiration pressure), which may be provided by console 102 or another device, and is used to pull tissue into the outer port 302 when the inner cutting surface 312 is located proximal to and away from the port 302. During operation of the vitrectomy probe 110, the inner cutting tube 214 moves in a reciprocal fashion (i.e., back-and-forth along the longitudinal axis LA of the probe 110) within the inner channel 306 of the outer cutting tube 212 to cut tissue that is pulled into the outer port 302 by the aspiration line.

Figure 5:
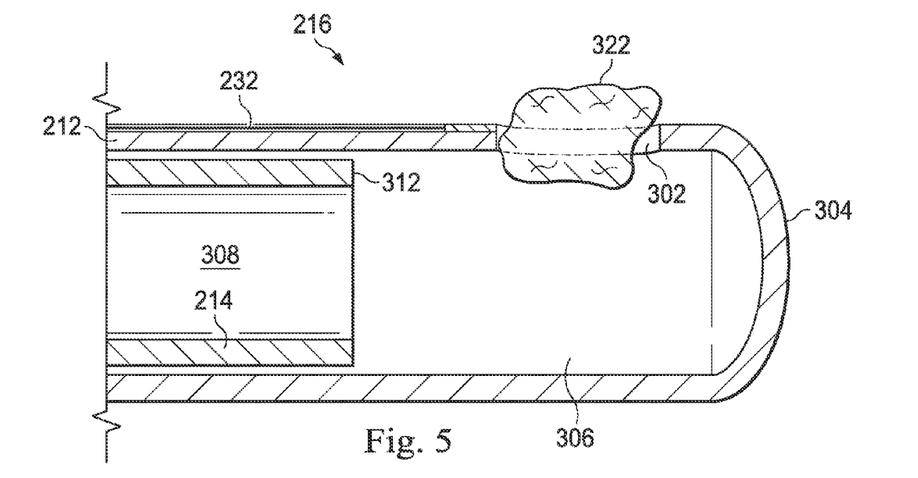
FIG. 5 is a close-up cross-sectional illustration of the exemplary distal portion of the cutter shown in FIG. 3 according to aspects of the present disclosure.

The processor 114 initiates or triggers the movement of the inner cutting tube 214 to cut tissue that is aspirated or drawn into the outer port 302. When used to cut tissue, upon actuation or signaling from the processor 114, the distal end 310 of inner cutting tube 214 is initially moved proximally away from the outer port 302 into a retracted position and the vacuum pressure pulls tissue into the outer port 302 and the inner channel 306. The distal end 310 of the inner cutting tube 214 then moves distally toward the outer port 302 into an extended position and severs the tissue within the inner channel 306 with the cutting surface 312. The severed tissue is pulled through the inner bore 308 of the inner cutting tube 214 by the aspiration system. The inner cutting tube 214 then moves proximally away from the outer port 302 into the retracted position (as shown in FIG. 5), and the cutting process is repeated. In some embodiments, without initiation or triggering (e.g., via signals or commands) from the processor 114, the motion inner cutting tube 214 would be arrested.

With reference now to both FIGS. 2 and 3, the inner cutting tube 214 is driven by air pressure directed on opposing sides of the diaphragm 220 (e.g., in response to control signals from the processor 114). In one example of operation, if air pressure is increased at the first port 202, the diaphragm 220 will move distally, displacing the inner cutting tube 214 relative to the outer cutting tube 212, thereby closing the tissue-receiving outer port 302 of the outer cutting tube 212. This cuts any material which may have been aspirated into the tissue-receiving outer port 302. Venting the pressure at the first port 202 and increasing the pressure at the second port 204 will move the diaphragm 220 proximally, opening the tissue-receiving outer port 302 so that it can draw in new material to be cut.

It's worth noting that other embodiments include alternative probe actuators. For example, some actuator embodiments include a piston motor in place of a diaphragm. In this type of embodiment, the cutter 210 is arranged so that movement of the piston also moves the inner cutting tube 214 of the cutter 210. Yet other actuator embodiments include other types of pneumatic or electric motors that drive the inner cutting tube 214.

Generally, for example in most vitrectomy procedures, the target ophthalmic tissues for aspiration and cutting are substantially transparent tissues such as, by way of non-limiting example, vitreous humor and transparent membranes. Non-target tissues are generally less transparent and more opaque than target tissues. However, because the cutter 210 operates extremely rapidly, with the inner cutting tube 214 moving within the outer cutting tube 212 at a very high rate, a surgeon cannot easily halt the operation of the cutter immediately upon aspiration of non-target tissue. Thus, non-target tissue (e.g., retinal tissue) may be aspirated into the outer port 302 and inadvertently cut by the cutter 210 during a vitrectomy procedure, which may cause unnecessary injury to the retina and/or other ocular structures.

By nature, the retina is very flexible and conformal, and therefore retinal tissue may be drawn by the vacuum source into the outer port 302, occluding the inner bore 308, preventing or limiting aspiration of the target tissue, and/or injuring the retina. In a healthy human eye, the retina is physically attached to the choroid in a generally circumferential manner. The vitreous humor, a transparent jelly-like material that fills the posterior segment of the eye, helps to cause the remainder of the retina to lie against, but not physically attach, to the choroid. A helpful analogy is to imagine the choroid as the walls of a fishbowl filled with vitreous humor. The retina is like a sheet of thin material that is pressed against the walls of the bowl by the vitreous humor, but is only physically attached to the walls at the rim of the bowl. If the vitrectomy probe 110 inadvertently cuts a portion of the retina, at least that portion of the retina may become detached from the choroid, which can cause vision loss and other adverse effects. Sometimes a portion of the retina will tear, allowing aqueous humor, and sometimes vitreous humor, to flow between the retina and the choroid, which also may result in a loss of vision. The tissue sensor 150 can assist the surgeon in avoiding the inadvertent cutting of non-target tissues such as the retina.

As mentioned above in relation to FIG. 1, the vitrectomy probe system 110 includes at least one tissue sensor 150. As shown in FIG. 2, the tissue sensor 150 is positioned within the cutter 210. In particular, the tissue sensor 150 is positioned in close proximity to the outer port 302 to enable the sensor 150 to measure (e.g., by detecting) a characteristic of the tissue aspirated into the outer port 302. The tissue sensor 150 comprises any type of sensor configured to sense a characteristic of the aspirated tissue that would enable the vitrectomy system 100 (e.g., the processor 114) to determine whether the tissue is a target tissue or a non-target tissue. For example, in one embodiment, the tissue sensor 150 comprises a fiberoptic sensor that can measure the degree of transparency (e.g., by detecting the amount of light that passes through the aspirated tissue) of the aspirated tissue. Other tissue characteristics that may be sensed by the tissue sensor 150 include, by way of non-limiting example, the amount of reflectivity, the electrical impedance, and/or indicators of the structural composition (e.g., layered or anamorphic) of the tissue.

In the embodiment pictured in FIGS. 2 and 3, the tissue sensor 150 is embedded in the outer cutting tube 212 and is configured to sense and measure (e.g., by detecting) a characteristic (e.g., the degree of transparency) of the tissue aspirated into the outer port 302. As depicted, the tissue sensor 150 is a fiber optic tissue sensor 150 coupled to electronics in the probe housing 230 as seen in FIG. 2 and/or the console 102 as seen in FIG. 1 by a sensor line 232. The sensor line 232 is configured to transfer the sensed data from the sensor 150 to electronics in the probe housing 230 and/or the processor 114 shown in FIG. 1. The sensor line 232 may be an electrical or a fiber optic line depending on the type of tissue sensor 150. In the pictured embodiment in FIGS. 2 and 3, both the tissue sensor 150 and the sensor line 232 are positioned within recesses formed in the outer cutting tube 212 so that the outer surface 235 of the outer cutting tube 212 remains smooth and uninterrupted. In some embodiments this recess is formed on the outside of the cutting tube 212, while in others it is formed on the inside, with an opening provided for the sensor 150 to access the aspirated tissue.

In the illustrated embodiment, the tissue sensor 150 is disposed distal to the system housing 230 and adjacent to the outer port 302. In the pictured embodiment, the tissue sensor 150 is positioned at the outer surface 235 of the outer cutting tube 212 in order to measure the tissue immediately as it enters the outer cutting tube 212. In other embodiments, the tissue sensor 150 can be positioned on an inner surface 240 of the outer cutting tube 212. In other embodiments, the tissue sensor 150 can be embedded entirely within the outer cutting tube 212 between the outer surface 235 and the inner surface 240. In each of these embodiments, the tissue sensor 150 is positioned with access to or exposure to an inner surface 237 of the outer bore 302 and insulation from the outer surface 235. Thus, the sensor 150 can measure by detecting characteristics of the tissue aspirated into the outer bore 302 while remaining shielded from the tissue immediately outside the outer cutting tube 212.

Figure 4:
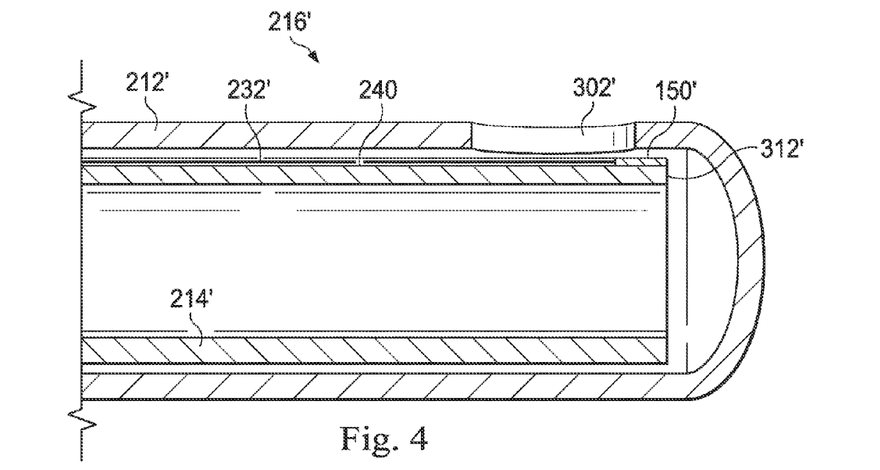
FIG. 4 is a close-up cross-sectional illustration of an exemplary distal portion of a cutter of a vitrectomy probe according to aspects of the present disclosure.

In other embodiments, as shown in FIG. 4, a tissue sensor 150' may be positioned on an outer surface 240 of an inner cutting tube 214'. FIG. 4 illustrates another exemplary distal portion 216' of a cutter 210'. The cutter 210' is substantially similar to the cutter 210 except for the differences described herein. In the pictured embodiment in FIG. 4, both the tissue sensor 150' and the sensor line 232' are positioned within recesses formed in the outer surface 240 of the inner cutting tube 214' so that the sensor 150 lies flush with the outer surface 240 and the outer surface 240 remains smooth and uninterrupted. In this embodiment, the tissue sensor 150' is positioned with access to or exposure to the outer surface 240 of the inner cutting tube 214'. Thus, the sensor 150' can measure characteristics of the tissue aspirated into the outer bore 302'. A sensor line 232' couples the tissue sensor 150' to electronics as discussed above in connection with the tissue sensor 150.

In some embodiments, the sensor recess is less than a thickness of the sensor 150 or more than the thickness of the sensor 150. The recess may be square shaped or any other shape suitable for receiving and housing the tissue sensor 150. Elongated recesses are provided for the electrical and/or optical supply lines.

Returning to FIG. 2, in the pictured embodiment, the vitrectomy probe 110 includes an arresting mechanism 320. The arresting mechanism 320 is configured to halt the cutting mechanism of the cutter 210 when the vitrectomy surgical system 100, based on the sensed data from the tissue sensor 150, concludes that the tissue (e.g., tissue 322 shown in FIG. 5) within the outer port 302 is not target tissue. In the pictured embodiment, the arresting mechanism 320 is disposed within the probe 110 adjacent to a proximal portion 325 of the cutter 210. As the inner cutting tube 214 is moved reciprocally within the outer cutting tube 212, the proximal portion 325 of the cutter 210 moves in unison with the inner cutting tube 214. The arresting mechanism may comprise any type of suitable element shaped and configured relative to the cutter 210 to arrest the motion of the proximal portion 325, and thereby halt the motion of the inner cutting tube 214 proximal to the outer port 302, as shown in FIG. 5. In one embodiment, the arresting mechanism 320 comprises a damper element configured to grasp the proximal portion 325 and halt the motion of the inner cutting tube 214. In another embodiment, the arresting mechanism 320 comprises a first fastening element shaped and configured to interact with (e.g., hook or snag) a corresponding second fastening element (not shown) on the proximal portion 325 to halt the motion of the inner cutting tube 214.

In some embodiments, the proximal portion 325 may comprise an aspiration line that is separable from the remainder of the cutter 210. In other embodiments, the proximal portion 325 comprises an integral part of the cutter 210. The arresting mechanism 325 may be disposed anywhere along the length of the cutter 210 (e.g., the proximal portion 325) that enables the arresting mechanism to halt the motion of the cutter 210. For example, in other embodiments, the proximal portion 325 may comprise a more proximal or a more distal portion of the cutter 210 than shown in FIG. 2.

The arresting mechanism 320 may be connected in a wired or wireless fashion to the console 102 and/or the processor 114. In the pictured embodiment, the arresting mechanism 320 is connected to the console 102 and/or the processor 114 via a communication cable 340. The communication cable 340 may extend from the console 102 into the vitrectomy probe 110 to the arresting mechanism 320. In some embodiments, the communication cable 340 is coupled to or forms part of the supply lines 102 shown in FIG. 1.

As described above, the tissue sensor 150 senses and measures (e.g., by detecting) a characteristic of the tissue aspirated into the outer port 302 and conveys that data to the processor 114. For example, in one embodiment, as tissue is drawn into the outer port 302, the tissue sensor 150 measures degree of transparency of the tissue and communicates that data to the processor 114 in the console 102 shown in FIG. 1. The processor 114 includes logic algorithms that use input data from the tissue sensor 150 to determine whether the sensed tissue is target tissue that should be cut or is non-target tissue that should not be cut. The processor 114 is operable to control the movement of the inner cutting member 214 based on the characteristic measured by the tissue sensor.

If the processor 114 determines, based on the input data, that the sensed tissue is non-target tissue, the processor 114 disables the cutting mechanism of the probe system 110 by either halting the motion of the inner cutting tube 214 (e.g., with the arresting mechanism 320) or preventing the actuation of the inner cutting tube 214 (e.g., by not initiating, triggering, or signaling the movement of the inner cutting tube 214). For example, in embodiments including the arresting mechanism 320, the processor 114 may signal, command, or activate the arresting mechanism 320 to halt the movement of the inner cutting tube 214 of the probe system 110.

In alternative embodiments, the vitrectomy probe 110 lacks the arresting mechanism 320. In such embodiments, if the processor 114, using the logic algorithm and the input data from the tissue sensor 150, determines that the tissue is non-target tissue that should not be cut, the processor 114 does not initiate, trigger, actuate, and/or signal the movement of the cutting mechanism of the probe system 110 (e.g., the triggering function of the processor 114). If the processor 114 does not initiate the cutting mechanism of the probe system, the probe system 110 cannot cut tissue.

In the pictured embodiment, the vitrectomy probe 110 includes an over-ride element 345, which may be the same as the over-ride element 126 shown in FIG. 1. The described features of the over-ride element 345 may also apply to the over-ride element 124 and/or 126. The over-ride element 345 comprises any of a variety of user input structures having ON/OFF functionality such as, by way of non-limiting example, a button, a dial, a switch, and a toggle. When activated or switched to an ON position, the over-ride element 345 enables the surgeon to over-ride the arresting mechanism of the vitrectomy surgical system 100 and/or to over-ride the triggering function of the processor 114. In particular, in embodiments including an arresting mechanism 320, when the over-ride element 345 is switched to an ON position, regardless of what type of tissue is aspirated into the outer port 302, the motion of the inner cutting tube 214 will not be halted by the arresting mechanism 320. For example, in one embodiment, when the over-ride element 345 is switched to an ON position, the arresting mechanism 320 is temporarily and reversibly disabled. In embodiments lacking an arresting mechanism 320, when the over-ride element 345 is switched to an ON position, regardless of what type of tissue is aspirated into the outer port 302, the motion of the inner cutting tube 214 will continue to be triggered by the processor 114. In other embodiments, when the over-ride element 345 is switched to an ON position, the tissue sensor 150 is temporarily and reversibly disabled.

The over-ride element 345 may be connected in a wired or wireless fashion to the console 102, the processor 114, and/or the arresting mechanism 320. In the pictured embodiment, the over-ride element 345 is connected to the console 102 and/or the processor 114 via a communication cable 350. The communication cable 350 may extend from the console 102 into the vitrectomy probe 110 to the over-ride element 345. In some embodiments, the communication cable 340 is coupled to or forms part of the supply lines 102 shown in FIG. 1. In some embodiments, the over-ride element 345 is additionally or alternatively connected to the arresting mechanism 320 via a communication cable 355.

Figure 6:
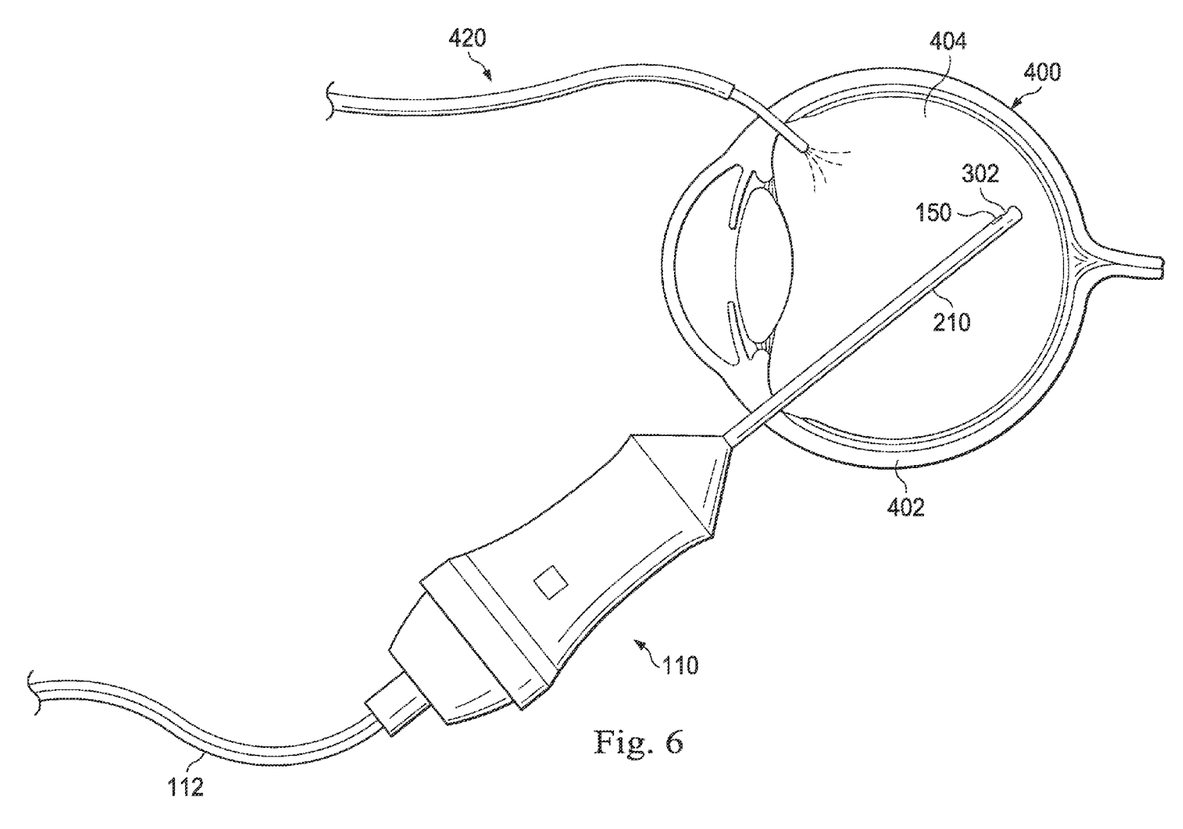
FIG. 6 is an illustration of a vitrectomy probe and an infusion line in situ in an eye according to exemplary aspects of the present disclosure.

FIG. 6 illustrates a partially cross-sectional view of an eye 400 undergoing a procedure involving the vitrectomy surgical system 100 and an infusion line or infusion cannula 420. During a vitrectomy procedure, a surgeon typically inserts the vitrectomy probe 110 into the posterior segment of the eye via an incision through the sclera in the pars plana. Such an incision is called a sclerotomy. The surgeon typically also inserts a fiber optic light source and the infusion cannula 420 into the eye via similar incisions, and may sometimes substitute an aspiration probe for the vitrectomy probe 110. While viewing the posterior segment under a microscope and with the aid of the fiber optic light source, the surgeon cuts and aspirates away vitreous using the vitrectomy probe 110 to gain access to the area of interest (e.g., the site of a retinal detachment or tear). The surgeon may also use the vitrectomy probe 110 to remove any membrane that has contributed to the retinal detachment or tear. During this portion of the surgery, a saline solution is typically infused into the eye via the infusion cannula 420 to maintain the appropriate intraocular pressure.

Both the vitrectomy probe 110 and the infusion line 420 may be coupled to a console, such as the console 102 shown in FIG. 1. In FIG. 6, the vitrectomy probe 110 and the infusion line 420 are inserted through the sclera 402 and into the vitreous chamber 404 of the eye 400. The infusion line 420 is a specialized type of probe used to deliver replacement fluid or irrigation fluid into the vitreous chamber 404 during vitrectomy procedures. A pressure level of the irrigation fluid may be increased or decreased by a surgical system.

In the illustrated embodiment, the vitrectomy probe 110 includes the tissue sensor 150 adjacent the outer port 302. As depicted, the tissue sensor 150 is positioned on the cutter 210 to measure a characteristic such as, by way of non-limiting example, the degree of transparency, of the tissue aspirated into the outer port 302. The data sensed by the tissue sensor 150 may be communicated to the console 102 and/or the processor 114 shown in FIG. 1 either wirelessly or via the supply lines 112. The tissue characteristics or data that may be sensed by the sensor 150 of the vitrectomy probe 110 facilitate improved control by the vitrectomy surgical system 100 of FIG. 1 by providing additional information that can be processed by the surgical system 100 (and/or the processor 114) and used for automated control of the cutter 210. For example, in one embodiment, by measuring and determining the transparency of the aspirated tissue, the vitrectomy surgical system 100 may be able to avoid the inadvertent cutting and removal of non-target tissue during a vitrectomy procedure by halting the motion of the inner cutting tube 214 before it cuts the tissue aspirated into the outer port 302 (as shown in FIG. 5).

The processor 114 shown in FIG. 1 may have user-settable or pre-defined limits for acceptable tissue characteristics or measurements that reflect target tissue characteristics. For example, in one embodiment where the tissue sensor 150 is configured to measure a degree of transparency of the tissue, the processor 114 may contain pre-defined or user-settable ranges defining the range of transparency associated with target tissues such as, by way of non-limiting example, vitreous and membranes (e.g., transparent tissues). The acceptable range of values corresponding to a desired target tissue may be modified before, during, or after a procedure. In embodiments including an arresting mechanism 320, when the tissue data sensed by the tissue sensor 150 exceeds the predetermined level of acceptable transparency (or other tissue characteristic) as a result of the aspiration of non-target tissue (e.g., retinal tissue) into the outer port 302, the processor 114 can signal the arresting mechanism 320 shown in FIG. 2 to halt the motion of the inner cutting tube 214 before it cuts the tissue 322 as shown in FIG. 5. In embodiments that lack the arresting mechanism 320, when the tissue data sensed by the tissue sensor 150 exceeds the predetermined level of acceptable transparency (or other tissue characteristic) as a result of the aspiration of non-target tissue (e.g., retinal tissue) into the outer port 302, the processor 114 does not initiate, signal, or trigger the movement of the inner cutting tube 214 and thereby prevents it from cutting the tissue 322 as shown in FIG. 5. For example, in some embodiments, the processor 114 suspends the motion of the inner cutting tube 214 (based upon the measured tissue characteristic) by halting the transmission of driving power to the inner cutting tube 214.

Figure 7:
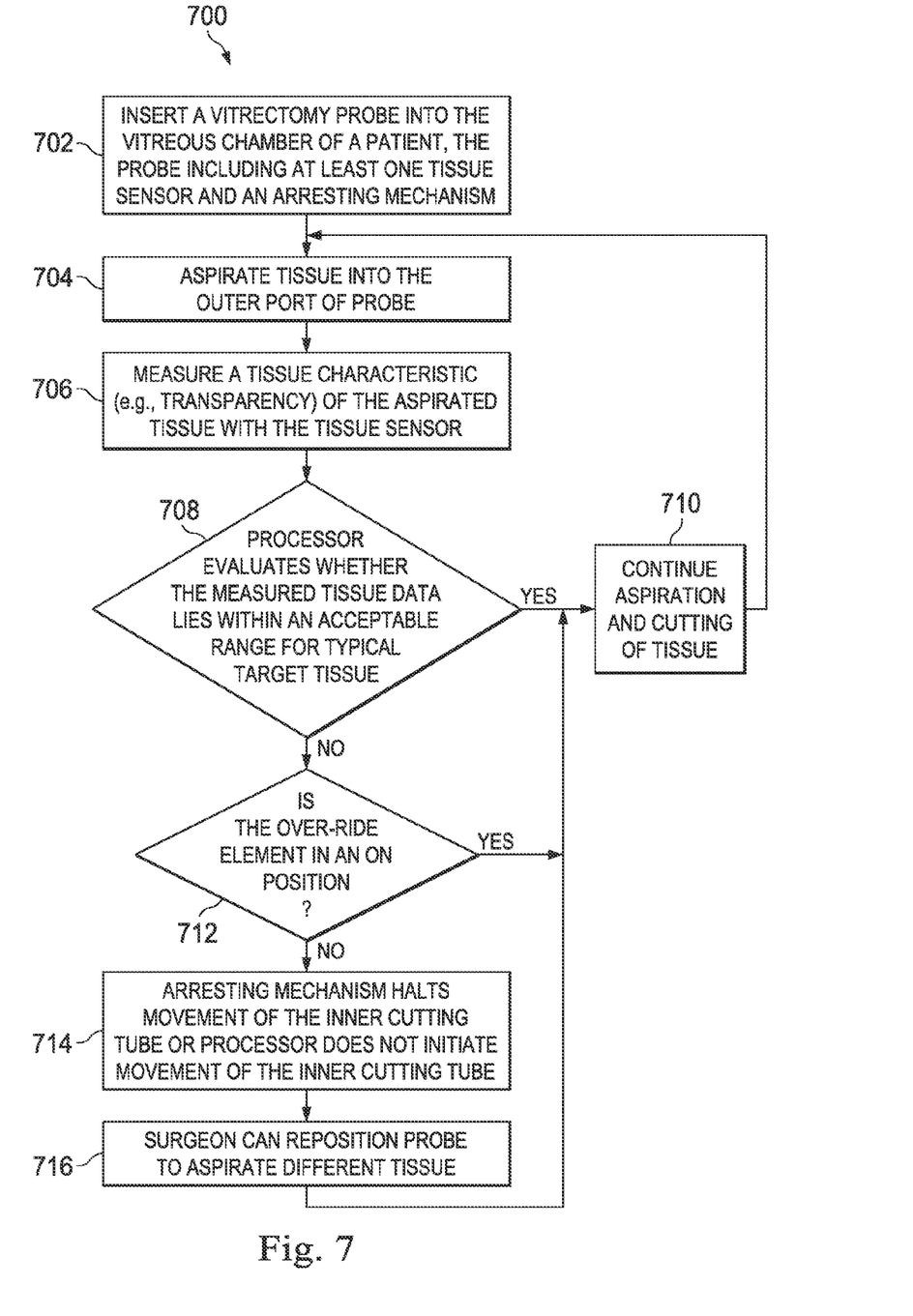
FIG. 7 is a flowchart showing a method of treating an ophthalmic condition according to exemplary aspects of the present disclosure.

However, if the surgeon desires to cut typically non-target (e.g., less transparent and more opaque tissue), the surgeon may adjust the over-ride element 345 shown in FIG. 2 (and/or the over-ride element 125 as shown in FIG. 1) to an ON position to allow the vitrectomy surgical system 100 to at least temporarily cut the typically non-target tissue. For example, in some instances, the surgeon may want the vitrectomy probe 110 to cut, aspirate, and remove certain tissues or materials, including without limitation, coagulated blood, debris, retinal tissue, and retinal pigment epithelium FIG. 7 is a flowchart of an exemplary method 700 of operating the vitrectomy surgical system 100 in treating an ophthalmic condition according to one embodiment of the present disclosure. As illustrated, the method 700 includes a number of enumerated steps, but embodiments of the method 700 may include additional steps before, after, and in between the enumerated steps. The illustrated embodiment begins at step 702 in which a surgeon inserts a probe (e.g., the vitrectomy probe 110) that includes at least one tissue sensor 150 and the arresting mechanism 320 through a sclera into a vitreous chamber of a patient. At step 704, the surgeon may aspirate tissue into the outer port 302 of the vitrectomy probe 110. At step 606, the tissue sensor 150 can measure a tissue characteristic (e.g., transparency) of the aspirated tissue by detecting the characteristic of the tissue and communicate data or signals representing the tissue characteristic to the console 102 (e.g., the processor 114).

At step 708, the processor 114 can evaluate whether the measured tissue data lies within the predetermined acceptable range of values for typical target tissue (e.g., vitreous humor and membranes). If the processor 114 determines that the tissue data lies within the predetermined range, then the system 100 continues to aspirate and cut the tissue at step 710. If, however, the processor 114 determines that the tissue data does not lie within the predetermined range, then, at step 712, the processor 114 queries whether the over-ride element 124 or 126 is in an ON position. If the over-ride element 124, 126 is in an ON position, then the system 100 continues to aspirate and cut the tissue at step 710. Thus, when the over-ride element 124, 126 is in the ON position, it prevents the processor 114 from controlling the movement of the inner cutting tube 214 based on the measured characteristic. If the over-ride element 124, 126 is in an OFF position, then, at step 714, the system 100 can prevent the cutting of the aspirated tissue within the outer port 302 at step 714 by either: (1) the arresting mechanism 320 halting the movement of the inner cutting tube 214, or (2) the processor 114 not initiating or triggering movement of the inner cutting tube 214.

In some embodiments, the processor 114 queries the ON/OFF status of the over-ride element 124 or 126 before step 706, and disables the tissue sensor 150 if the over-ride element is in the ON position (thereby avoiding steps 706 and 708 and continuing directly to step 710). In other embodiments, the processor 114 queries the ON/OFF status of the over-ride element 124 or 126 immediately after step 706, and disables the arresting mechanism 320 (or continues to trigger movement of the inner cutting tube 214) if the over-ride element is in the ON position (thereby avoiding step 708 and continuing directly to step 710). After the movement of the inner cutting tube 214 has been prevented at step 714, the surgeon may reposition the probe 110 to aspirate a different portion of tissue at steps 716 and 710. At any time before, during, or after the procedure, the surgeon may readjust the over-ride element 124, 126 to turn it ON or OFF.

The systems and methods disclosed herein may be used to enable better performance of vitrectomy surgical systems by enabling focal tissue measurements during a vitrectomy procedure that help the system determine in real-time whether or not aspirated tissue within the vitrectomy probe should be cut, aspirated, and removed. This additional level of control may enable a surgeon to avoid inadvertently cutting and removing typically non-target tissues (e.g., retinal tissue). This may result in more effective vitrectomy procedures and reduced risk of ocular injury, thereby improving the overall clinical result.

Persons of ordinary skill in the art will appreciate that the embodiments encompassed by the present disclosure are not limited to the particular exemplary embodiments described above. In that regard, although illustrative embodiments have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A device for removing a tissue from an eye of a patient during a medical procedure, the device comprising:
    a housing;
    a cutter extending from a distal end of the housing along a longitudinal axis, the cutter comprising:
        an outer cutting tube coupled to the housing, the outer cutting tube including an outer surface and an inner surface;
        an outer port formed in the outer cutting tube, the outer port comprising an aperture extending from the outer surface to the inner surface of the outer cutting tube, the outer port sized to receive the tissue;
        an inner cutting tube disposed within the outer cutting tube, the inner cutting tube having a distal tube end slidable along the longitudinal axis between a retracted position proximal to the outer port and an extended position distal to the outer port; and
    a tissue sensor positioned on the cutter and configured to measure a characteristic of the tissue received within the outer port to identify when the tissue entering the outer port is non-target tissue and when the tissue entering the outer port is target tissue;
    an actuator positioned within the housing and configured to reciprocate the inner cutting tube to slide the distal tube end between the retracted position and the extended position to open and close the outer port and cut the tissue; and
    an arresting mechanism comprising a component configured to selectively halt or allow motion of the inner cutting tube relative to the outer cutting tube depending on whether the non-target tissue is detected by the tissue sensor;
    wherein the arresting mechanism comprises a first fastening element shaped and configured to interact with a second fastening element disposed on a proximal portion of the cutter within the housing to halt motion of the inner cutting tube in the retracted position.

2. The device of claim 1, wherein the tissue sensor is disposed adjacent to the outer port on the outer cutting tube.

3. The device of claim 2, wherein the tissue sensor is disposed within a recess on a cylindrical surface of the outer cutting tube.

4. The device of claim 2, wherein the tissue sensor is disposed within a recess embedded within a cylindrical surface of the outer cutting tube between the inner and outer surfaces of the outer cutting tube.

5. The device of claim 1, wherein the tissue sensor is disposed within a recess on an outer surface of the inner cutting tube.

6. The device of claim 1, wherein the tissue sensor comprises a fiber-optic sensor configured to measure a degree of transparency of the tissue.

7. The device of claim 1, wherein the tissue sensor comprises a fiber-optic sensor configured to measure reflectivity of the tissue.

8. The device of claim 1, wherein the arresting mechanism is positioned within the housing and is configured to selectively halt motion of the inner cutting tube in the retracted position during the medical procedure.

9. The device of claim 1, further including an over-ride element comprising a user input structure that is adjustable between an ON position and an OFF position.

10. The device of claim 9, wherein the over-ride element in the ON position is configured to disable the arresting mechanism such that motion of the inner cutting tube is allowed regardless of a type of tissue detected by the tissue sensor.

11. The device of claim 9, wherein the over-ride element in the ON position is configured to disable the tissue sensor.

* * * * *